(12) United States Patent
Yamada (10) Patent No.: US 8,975,587 B2
(45) Date of Patent: Mar. 10, 2015

(54) POSITRON CT APPARATUS AND A RECONSTRUCTION METHOD

(75) Inventor: Yoshihiro Yamada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 94 days.

(21) Appl. No.: 13/980,865

(22) PCT Filed: Feb. 15, 2012

(86) PCT No.: PCT/JP2012/000992
§ 371 (c)(1),
(2), (4) Date: Jul. 19, 2013

(87) PCT Pub. No.: WO2012/120791
PCT Pub. Date: Sep. 13, 2012

(65) Prior Publication Data
US 2013/0299708 A1     Nov. 14, 2013

(30) Foreign Application Priority Data
Mar. 10, 2011 (JP) ................. 2011-052952

(51) Int. Cl.
| | | |
|---|---|---|
| *G01T 1/164* | (2006.01) | |
| *A61B 5/00* | (2006.01) | |
| *A61B 6/03* | (2006.01) | |
| *G01T 1/29* | (2006.01) | |
| *A61B 6/00* | (2006.01) | |

(52) U.S. Cl.
CPC ............ *A61B 5/0033* (2013.01); *G01T 1/1647* (2013.01); *A61B 6/037* (2013.01); *G01T 1/164* (2013.01); *G01T 1/2985* (2013.01); *A61B 6/508* (2013.01)
USPC ..................... 250/363.03; 382/131

(58) Field of Classification Search
USPC ..................... 250/363.03; 382/131
See application file for complete search history.

(56) References Cited

U.S. PATENT DOCUMENTS

| 6,194,728 | B1 * | 2/2001 | Bosnjakovic ............ 250/370.11 |
| 7,840,052 | B2 * | 11/2010 | Zhao et al. .................. 382/131 |
| 8,063,379 | B2 * | 11/2011 | Suhami .................. 250/370.09 |
| 2008/0128631 | A1 * | 6/2008 | Suhami .................. 250/370.09 |
| 2010/0080339 | A1 * | 4/2010 | Austin et al. ..................... 378/4 |
| 2010/0243907 | A1 * | 9/2010 | Jansen et al. ............. 250/370.09 |

OTHER PUBLICATIONS

Nakayama et al., "Derivation and implementation of ordered-subsets algorithms for list-mode PET data", IEEE Nuclear Science Symposium Conference Record: pp. 1950-1954, 2005.

(Continued)

*Primary Examiner* — David Porta
*Assistant Examiner* — Djura Malevic
(74) *Attorney, Agent, or Firm* — McDermott Will & Emery LLP (57) ABSTRACT

When calculating a system matrix (detection probability), adjustment is made by fitting a point spread function (PSF) expressed by a Gauss function to a profile of count values of radiation with respect to a distance from a point source which emits radiation of the same type as the positron-emitting drug, and a distance range of the above PSF is adjusted for each layer in a depth direction of gamma-ray detectors indicating an incident direction in which the radiation strikes. By calculating the system matrix (detection probability) after adjusting the distance range of the function for each layer, improvement can be made in image quality of a reconstructed image.

21 Claims, 8 Drawing Sheets

(56) References Cited

OTHER PUBLICATIONS

Panin et al., "Fully 3-D PET reconstruction with system matrix derived from point source measurements", IEEE Transactions on Medical Imaging, vol. 25, Issue: 7, pp. 907-921, Jul. 2006.

Tanaka et al., "Subset-dependent relaxation in block-iterative algorithms for image reconstruction in emission tomography", Phys Med Biol 48, pp. 1405-1422, 2003.

Reader et al., "EM algorithm system modeling by image-space techniques for PET reconstruction", IEEE Transactions on Nuclear Science, vol. 50, pp. 1392-1396, 2003.

Tonami et al., "Sophisticated 32×32×4-layer DOI Detector for High Resolution PEM Scanner", IEEE Medical Imaging Conference Record, pp. 3803-3807, 2007.

International Search Report issued in International Application No. PCT/JP2012/000992 mailed May 15, 2012.

* cited by examiner

POSITRON CT APPARATUS AND A RECONSTRUCTION METHOD

RELATED APPLICATIONS

This application is the U.S. National Phase under 35 U.S.C. §371 of International Application No. PCT/JP2012/000992, filed on Feb. 15, 2012, which in turn claims the benefit of Japanese Application No. 2011-052952, filed on Mar. 10, 2011, the disclosures of which Applications are incorporated by reference herein.

TECHNICAL FIELD

This invention relates to a positron CT apparatus and a reconstruction method for detecting radiation released from a positron-emitting drug introduced into the body of a subject and generating a positron distribution image as an image.

BACKGROUND ART

A positron CT apparatus, i.e. a PET (Positron Emission Tomography) apparatus, is constructed to detect two gamma rays generated by annihilation of positive electrons (positrons), and reconstruct an image of the subject only when a plurality of detectors detect gamma rays at the same time (that is, only when coincidences are counted).

With this PET apparatus, quantitative measurement of various living body functions is possible by serially measuring a process of drug accumulation in target tissue after introducing a radioactive drug into the subject. Therefore, images obtained by the PET apparatus have functional information.

Specifically, to describe this by taking a small animal (e.g. a mouse) as an example of subject, a positron (positive electron) emitting isotope (e.g. $^{15}O$, $^{18}F$, $^{11}C$, or the like) is injected into the body of the subject, and gamma rays generating when the positrons released from these combine with electrons are detected. The detection of these gamma rays is carried out with a detector array consisting of numerous gamma-ray detectors. And a computer carries out image reconstruction to create images of the subject.

The following technique is used when reconstructing images (see Nonpatent Documents 1 and 2, for example). First, pixels formed of 3D voxels in a field of view (FOV) are expressed by $v_j$ (j=0, 1, ..., J−1), and an i-th LOR (Line Of Response) by $L_i$ (i=0, 1, ..., I−1). LOR refers to a virtual straight line linking two detectors that carry out coincidence counting. Where pixels consist of 3D voxels, LOR refers to a tubular region linking two detectors having detected two gamma-ray photons generating from each voxel and emitted in opposite directions.

Now, in reconstruction of a PET image, probability $a_{ij}$ that gamma-ray photons generating from voxels $v_j$ will be detected on LOR ($L_i$) plays an important role. This $a_{ij}$ is called "system matrix". See Nonpatent Documents 1 and 2 for formulization of image reconstruction.

The number (count value) of photons is measured using a point source which emits the same type of radiation as a positron-emitting drug. A profile of the number of photons with respect to distances from the point source is obtained, and is adjusted by fitting it to a Gauss function or the like, thereby to obtain a point spread function (PSF). Then, can be obtained by assuming that detection probability is proportional to the point spread function (hereinafter abbreviated to "PSF" as appropriate) (see Nonpatent Document 3, for example).

However, when the PSF obtained from the fitting is used as it is, an overcorrection phenomenon (e.g. ringing adjacent boundaries of the subject) appears due to errors in geometric calculations in the reconstruction calculations, or statistical errors included in the data for reconstruction. It is known that, in order to inhibit this overcorrection phenomenon, $a_{ij}$ needs to be calculated by narrowing by a fixed quantity the spread of the PSF obtained from actual measurement (see Nonpatent Document 4, for example).

Specifically, the distance range of the PSF may be adjusted by adjusting to change the full width at half maximum (FWHM) or distribution of the Gauss function. When the Gauss function is expressed by $\alpha \exp\{-(x-b)^2/2c^2\}$, the full width at half maximum (FWHM) is a value of an entire width corresponding to a half value of local maximal value (peak) of the Gauss function, which is expressed by $2\sqrt{(2 \ln 2)} \cdot c$.

Incidentally, in recent years, in order to improve the spatial resolution of images, detectors consisting of scintillator elements arranged in three dimensions have been used in PET apparatus (see Nonpatent Document 5, for example). Specifically, a PET apparatus has, incorporated therein, DOI detectors which can discriminate positions in depth directions (DOI: Depth of Interaction) where interaction has occurred. The DOI detectors are constructed by stacking scintillator elements in the depth directions of radiation (gamma rays here), and coordinate information on the depth directions and transverse directions (directions parallel to the planes of incidence) which caused the interaction is obtained by centroid calculation. By using the DOI detectors, it becomes possible to inhibit resolution degradation at peripheries of the field of view.

PRIOR ART DOCUMENTS

Nonpatent Documents

[Nonpatent Document 1]
Nakayama T, Kudo H: Derivation and implementation of ordered-subsets algorithms for list-mode PET data, IEEE Nuclear Science Symposium Conference Record: 1950-1954, 2005

[Nonpatent Document 2]
Tanaka E, Kudo H: Subset-dependent relaxation in block-iterative algorithms for image reconstruction in emission tomography. In: Phys Med Biol 48, 1405-1422, 2003

[Nonpatent Document 3]
Panin V. Y. et al., "Fully 3-D PET Reconstruction with system matrix derived from point source measurements," IEEE Trans. on Med. Img., vol. 25, no. 7 pp. 907-921, July 2006.

[Nonpatent Document 4]
Reader et al., "EM algorithm system modeling by image-space techniques for PET reconstruction," IEEE Trans. on Nucl Sci vol. 50, pp. 1392-1396, 2003.

[Nonpatent Document 5]
H. Tonami, K. Kitamura, M. Satoh, T. Tsuda, and Y. Kumazawa, "Sophisticated 32×32×4-Layer DOI Detector for High Resolution PEM Scanner," IEEE Medical Imaging Conference Record, pp. 3803-3807, 2007.

DISCLOSURE OF THE INVENTION

Problem to be Solved by the Invention

However, the way of obtaining $a_{ij}$ described in Nonpatent Documents 3 and 4 noted above is aimed at the detectors consisting of scintillator elements arranged in two dimensions (in other words, in one layer). It has become clear that, in the case of DOI detectors consisting of scintillator elements arranged in three dimensions as in Nonpatent Document 5 noted above, only narrowing by a fixed quantity the spread of PSFs which is a target of fitting when calculating $a_{ij}$ cannot reflect layer differences.

This invention has been made having regard to the state of the art noted above, and its object is to provide a positron CT apparatus and a reconstruction method which can improve the image quality of reconstructed images.

Means for Solving the Problem

To fulfill the above object, this invention provides the following construction.

A positron CT apparatus according to this invention has a plurality of detectors for detecting radiation released from a positron-emitting drug given to a subject, and outputting electric signals; a coincidence counting circuit for detecting, based on the electric signals, that a simultaneous observation of the radiation is made in two of the detectors; a system matrix calculating device for calculating a system matrix based on outputs of the coincidence counting circuit; and a reconstructing device for generating a distribution image of the positrons as an image based on the system matrix; the positron CT apparatus comprising a function adjusting device for making adjustment by fitting a point spread function expressed to a profile of count values of radiation with respect to a distance from a point source which emits radiation of the same type as the positron-emitting drug; and a distance range adjusting device for adjusting a distance range of the function for each layer in a depth direction of the detectors indicating an incident direction in which the radiation strikes; wherein the system matrix is calculated based on the function with the distance range adjusted.

[Functions and Effects] With the positron CT apparatus according to this invention, when calculating a system matrix (detection probability $a_{ij}$), the function adjusting device makes adjustment by fitting a point spread function to a profile of count values of radiation with respect to a distance from a point source which emits radiation of the same type as the positron-emitting drug, and the distance range adjusting device adjusts a distance range of the above function for each layer in a depth direction of the detectors indicating an incident direction in which the radiation strikes. Considering that the spread of counts of the radiation changes for each layer, the gap is thought to decrease by adjusting the distance range (e.g. full width at half maximum (FWHM) or distribution) of the point spread function. Thus, image quality of a reconstructed image can be improved by adjusting the distance range of the function for each layer to obtain the system matrix (detection probability $a_{ij}$).

A reconstruction method according to this invention is a reconstruction method for generating a distribution image of positrons as an image based on radiation released from a positron-emitting drug given to a subject, the reconstruction method comprising a series of (a) a function adjusting step for making adjustment by fitting a point spread function to a profile of count values of radiation with respect to a distance from a point source which emits radiation of the same type as the positron-emitting drug; (b) a distance range adjusting step for adjusting a distance range of the function for each layer in a depth direction of detectors indicating an incident direction in which the radiation strikes; (c) a system matrix calculating step for calculating a system matrix based on the function with the distance range adjusted; and (d) a reconstructing step for generating the distribution image of the positrons as an image based on the system matrix.

[Functions and Effects] With the reconstruction method according to this invention, when calculating a system matrix (detection probability $a_{ij}$), the function adjusting step makes adjustment by fitting a point spread function to a profile of count values of radiation with respect to a distance from a point source which emits radiation of the same type as the positron-emitting drug, and the distance range adjusting step adjusts a distance range of the above function for each layer in a depth direction of the detectors indicating an incident direction in which the radiation strikes. Thus, image quality of a reconstructed image can be improved by adjusting the distance range of the function for each layer to obtain the system matrix (detection probability $a_{ij}$).

In the above reconstruction method, in order to take into consideration the larger statistical errors occur with geometric calculations and reconstruction data at the time of reconstruction for the deeper layers in the depth direction of the detectors, it is preferred that the adjustment is made by reducing the distance range by a progressively larger extent for positions becoming deeper in the depth direction of the detectors. That is, it is thought that the spread of counts of the radiation is small for layers shallow in the depth direction of the detectors, and that the spread of counts of the radiation is large for layers deep in the depth direction. Therefore, the gap is thought to decrease when the distance range is not adjusted, or the distance range is adjusted by slightly reducing it, for layers shallow in the depth direction of the detectors, and the distance range is adjusted by reducing it by a progressively large extent for positions becoming deeper in the depth direction of the detectors.

In the above reconstruction method, based on results of reconstruction of each layer in the depth direction of the detectors, the distance range adjusting step adjusts the distance range of the function for each layer.

In the positron CT apparatus and the reconstruction method, the point spread function is expressed by a Gauss function.

Effects of the Invention

With the positron CT apparatus and reconstruction method according to this invention, when calculating a system matrix (detection probability $a_{ij}$), adjustment is made by fitting a point spread function to a profile of count values of radiation with respect to a distance from a point source which emits radiation of the same type as the positron-emitting drug, and a distance range of the above function is adjusted for each layer in a depth direction of detectors indicating an incident direction in which the radiation strikes. By calculating the system matrix (detection probability $a_{ij}$) after adjusting the distance range of the function for each layer, improvement can be made in image quality of a reconstructed image.

BRIEF DESCRIPTION OF THE DRAWINGS

FIGS. 8 (a) and (b) are schematic views illustrating adjustment of a distance range of the point spread function (PSF);

EMBODIMENTS

An embodiment of this invention will be described hereinafter with reference to the drawings.

Figure 1:
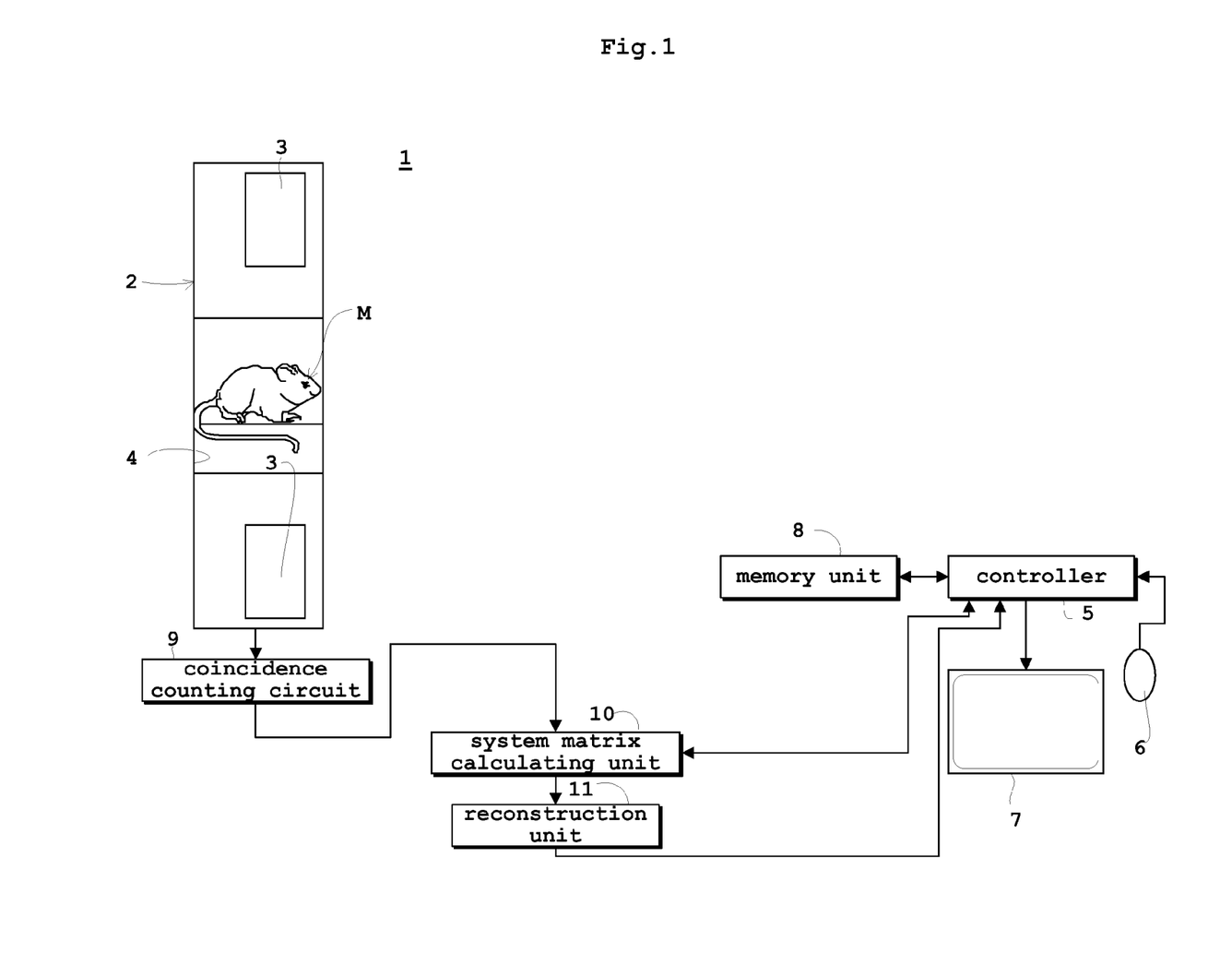
FIG. 1 is a side view and block diagram of a PET (Positron Emission Tomography) apparatus according to an embodiment.
Figure 2:
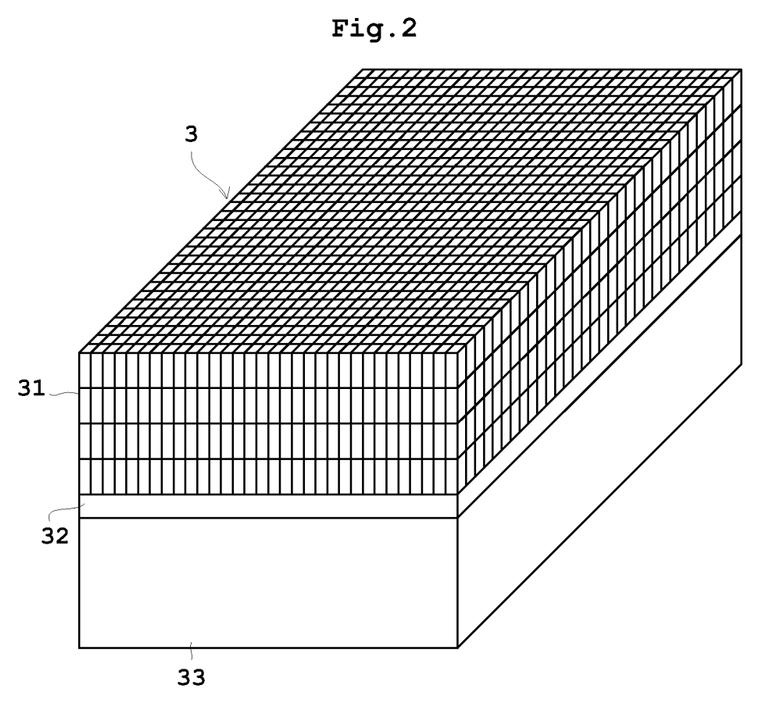
FIG. 2 is an outline perspective view of a gamma-ray detector.

FIG. 1 is a side view and block diagram of a PET (Positron Emission Tomography) apparatus according to the embodiment. FIG. 2 is an outline perspective view of a gamma-ray detector. This embodiment will be described taking a small animal (e.g. a mouse) as an example of subject, and taking a PET apparatus for small animals as an example of PET apparatus.

The PET apparatus 1 according to this embodiment, as shown in FIG. 1, includes a gantry 2 for receiving a subject M, and gamma-ray detectors 3. The gamma-ray detectors 3 are arranged in a ring form to surround the subject M, and are embedded in the gantry 2 (see also FIG. 5). The gantry 2 has an opening 4 for receiving the subject M. The gamma-ray detectors 3 correspond to the detectors in this invention.

In addition, the PET apparatus 1 according to this embodiment includes a controller 5, an input unit 6, an output unit 7, a memory unit 8, a coincidence counting circuit 9, a system matrix calculating unit 10, and a reconstruction unit 11. The input unit 6 corresponds to the function adjusting device and the distance range adjusting device in this invention. The coincidence counting circuit 9 corresponds to the coincidence counting circuit in this invention. The system matrix calculating unit 10 corresponds to the system matrix calculating device in this invention. The reconstruction unit 11 corresponds to the reconstructing device in this invention.

The controller 5 performs overall control of the components forming the PET apparatus 1 according to this embodiment. The controller 5 is formed of a central processing unit (CPU) and the like.

The input unit 6 feeds data and commands inputted by the operator into the controller 5. The input unit 6 is formed of pointing devices represented by a mouse, keyboard, joystick, trackball, touch panel and so on. The output unit 7 is formed of a display unit represented by a monitor, a printer and the like. In this embodiment, the operator carries out fitting (adjustment) of a PSF manually by inputting through the input unit 6 a value of each parameter of the point spread function (PSF) expressed by a Gauss function described hereinafter. The operator adjusts a distance range manually by inputting through the input unit 6 a value of adjustment of a distance range of the PSF. In this embodiment, therefore, the input unit 6 has also the function of the function adjusting device and the function of the distance range adjusting device in this invention.

The memory unit 8 is formed of storage media represented by a ROM (Read-only Memory), RAM (Random-Access Memory) and so on. In this embodiment, data relating to coincidence counting such as values of coincidence counting (counts) given by the coincidence counting circuit 9, detector pairs each consisting of two gamma-ray detectors 3 having counted coincidences, and LORs, a value of each parameter of the PSF and a value of adjustment of the distance range of the PSF inputted through the input unit 6, a system matrix calculated by the system matrix calculating unit 10, and images processed by the reconstruction unit 11, are written to and stored in the RAM and are read from the RAM as necessary. The ROM stores beforehand programs for imaging, including various types of nuclear medicine diagnosis, for example. The programs are executed by the controller 5 to carry out nuclear medicine diagnoses corresponding to the programs, respectively.

The system matrix calculating unit 10 and reconstruction unit 11 are realized, for example, by the controller 5 executing the programs stored in the ROM of the storage media represented by the above memory unit 8, or the commands inputted by the pointing devices represented by the input unit 6.

Scintillator blocks 31 (see FIG. 2) of each gamma-ray detector 3 convert into light gamma rays generating from the subject M medicated with a radioactive drug. A photomultiplier tube (PMT) 33 (see FIG. 2) of the gamma-ray detector 3 multiplies the converted light and converts it into an electric signal. The electric signal is inputted to the coincidence counting circuit 9 as image information (pixel value, i.e. count of coincidences counted by the gamma-ray detector 3).

Specifically, when the subject M is medicated with the radioactive drug, two gamma rays will be generated by annihilation of a positron of a positron-emitting RI. The coincidence counting circuit 9 checks positions of the scintillator blocks 31 (see FIG. 2) and incidence timing of the gamma rays, and determines the inputted image information to be proper data only when the gamma rays impinge on two scintillator blocks 31 at opposite sides of the subject M at the same time. When a gamma ray impinges on only one scintillator block 31, the coincidence counting circuit 9 discards it. That is, the coincidence counting circuit 9 detects, based on the above electric signals, that gamma rays are observed simultaneously by two gamma-ray detectors 3.

The image information inputted to the coincidence counting circuit 9 is inputted to the system matrix calculating unit 10 and reconstruction unit 11. The reconstruction unit 11 carries out reconstruction based on the system matrix calculated by the system matrix calculating unit 10, to obtain images of the subject M. Specifically, based on the system matrix, the reconstruction unit 11 generates positron distribution images as images. The images are sent to the output unit 7 through the controller 5. Thus, a nuclear medicine diagnosis is carried out based on the images obtained by the reconstruction unit 11. Specific functions of the input unit 6, system matrix calculating unit 10 and reconstruction unit 11 will be described hereinafter.

The gamma-ray detector 3, as shown in FIG. 2, has scintillator blocks 31, a light guide 32 optically coupled to the scintillator blocks 31, and a photomultiplier tube (hereinafter abbreviated to "PMT") 33 optically coupled to the light guide 32. Each scintillator element forming the scintillator blocks 31 converts a gamma ray into light by emitting light in response to incidence of the gamma ray. The scintillator element detects the gamma ray through this conversion. The light emitted from the scintillator element is fully diffused in the scintillator blocks 31, and inputted to the PMT 33 through the light guide 32. The PMT 33 multiplies the light converted by the scintillator blocks 31, and converts it into an electric signal. The electric signal is sent as image information (pixel value) to the coincidence counting circuit 9 (see FIG. 1) as described above.

The gamma-ray detector 3, as shown in FIG. 2, is a DOI detector having scintillator elements arranged three-dimensionally and forming a plurality of layers in the depth direction. While FIG. 2 shows a DOI detector with four layers, there is no limitation as to the number of layers as long as it is plural.

Figure 3:
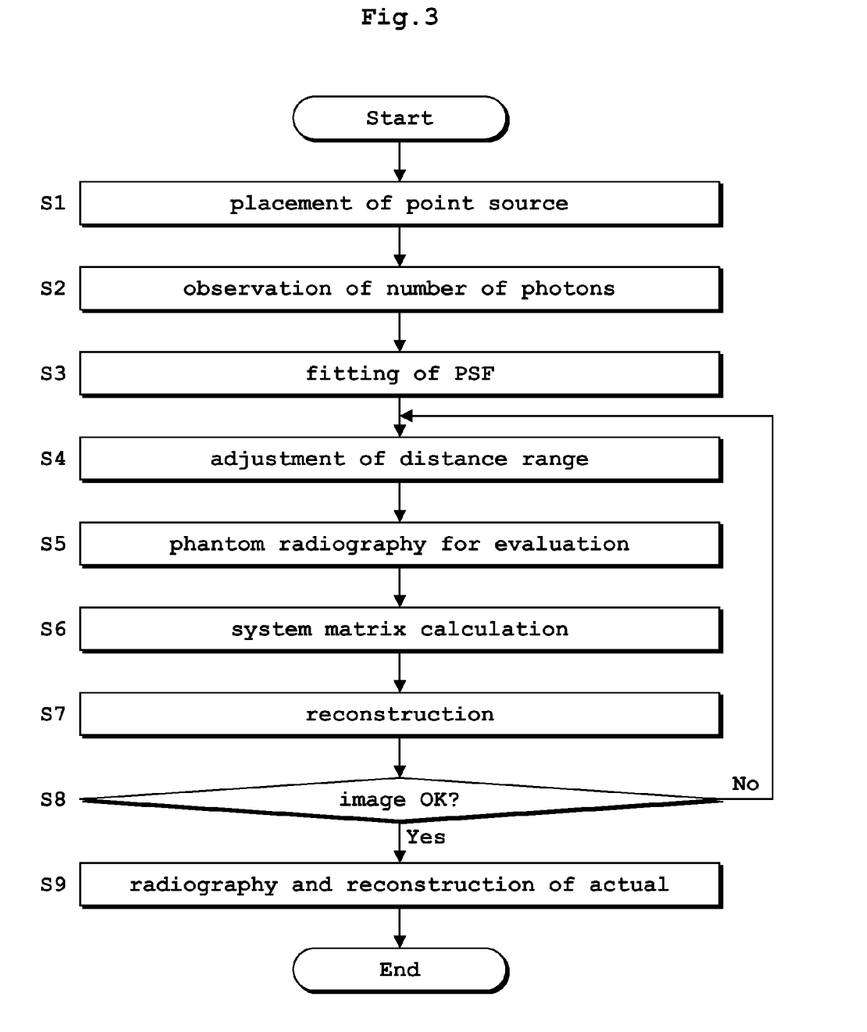
FIG. 3 is a flow chart showing a sequence of a reconstruction method including a reconstructing step.
Figure 4:
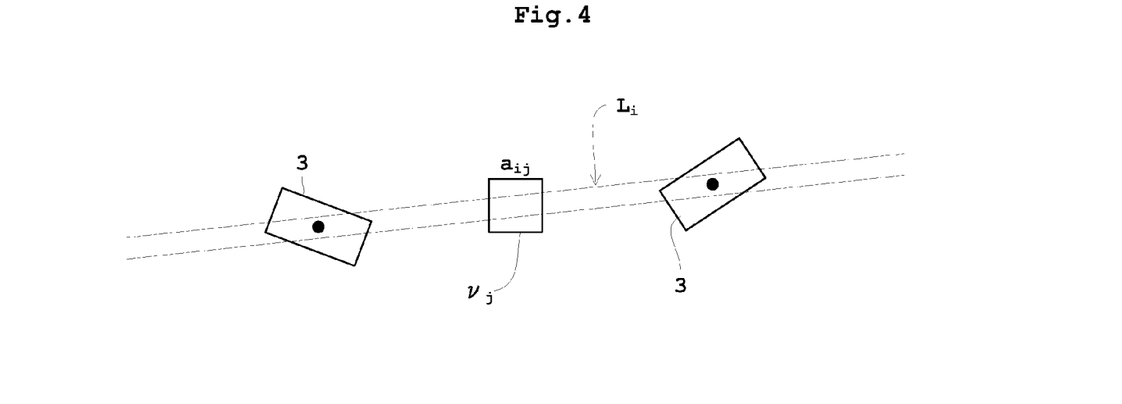
FIG. 4 is a schematic view showing coincidence counting in gamma-ray detectors, which illustrates detection probability.
Figure 5:
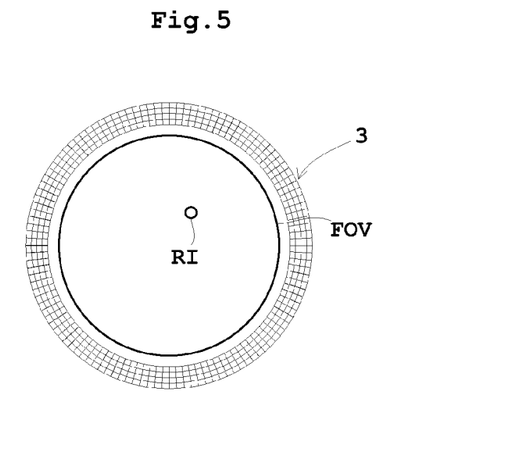
FIG. 5 is a schematic view showing a positional relationship with the gamma-ray detectors when a point source is disposed.
Figure 6:
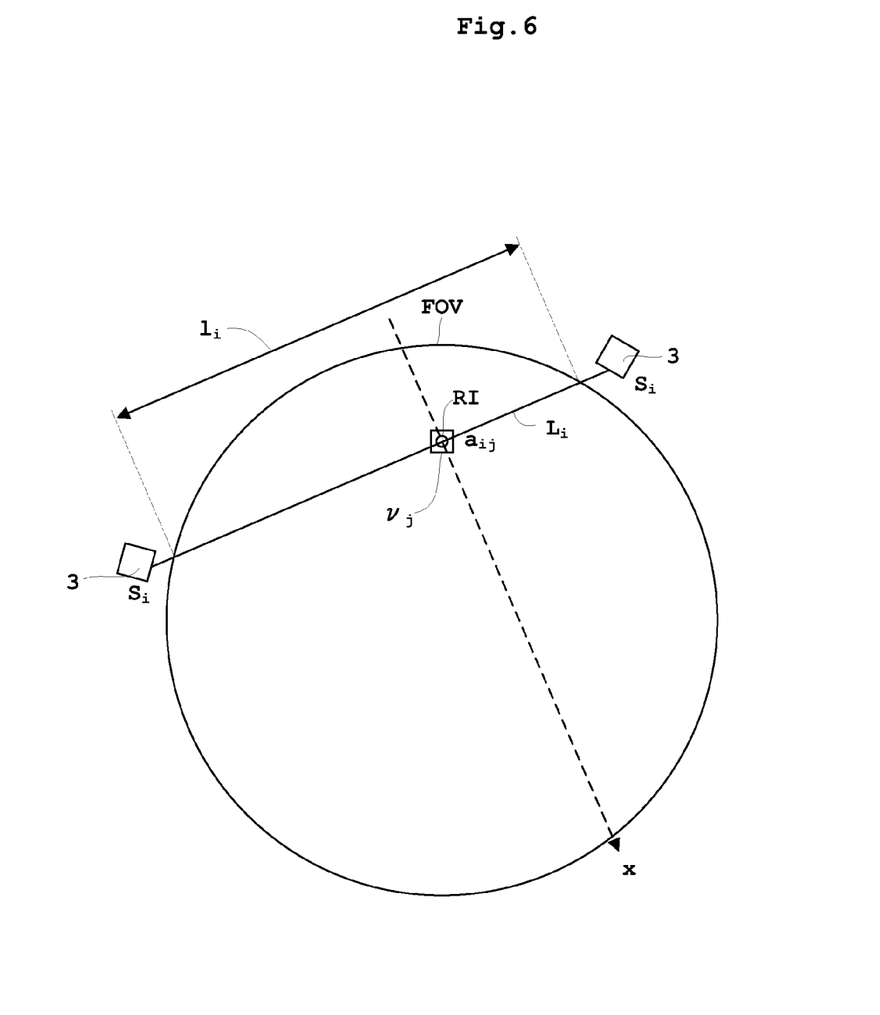
FIG. 6 is a schematic view illustrating distances from the gamma-ray detectors, voxels, LORs and point source when the point source is drawn together.
Figure 7:
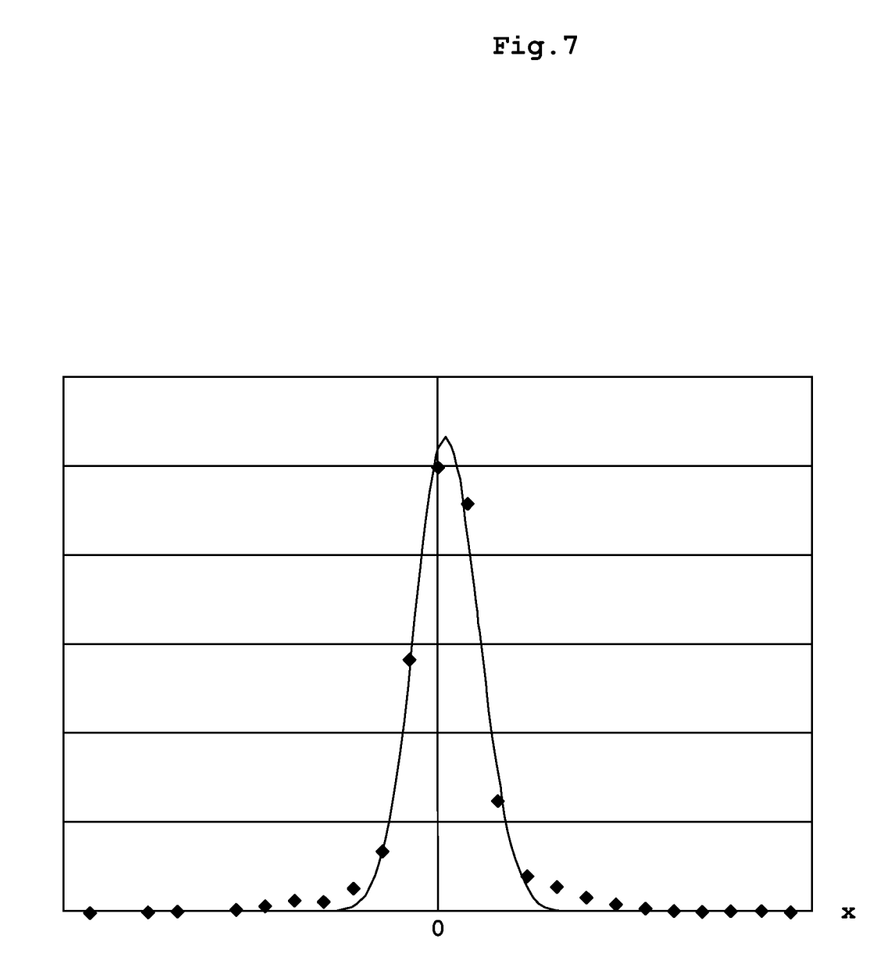
FIG. 7 is a graph of a profile of the number (count value) of photons with respect to the distances from the point source and results of fitting (adjustment) of a point spread function (PSF)
Figure 8:
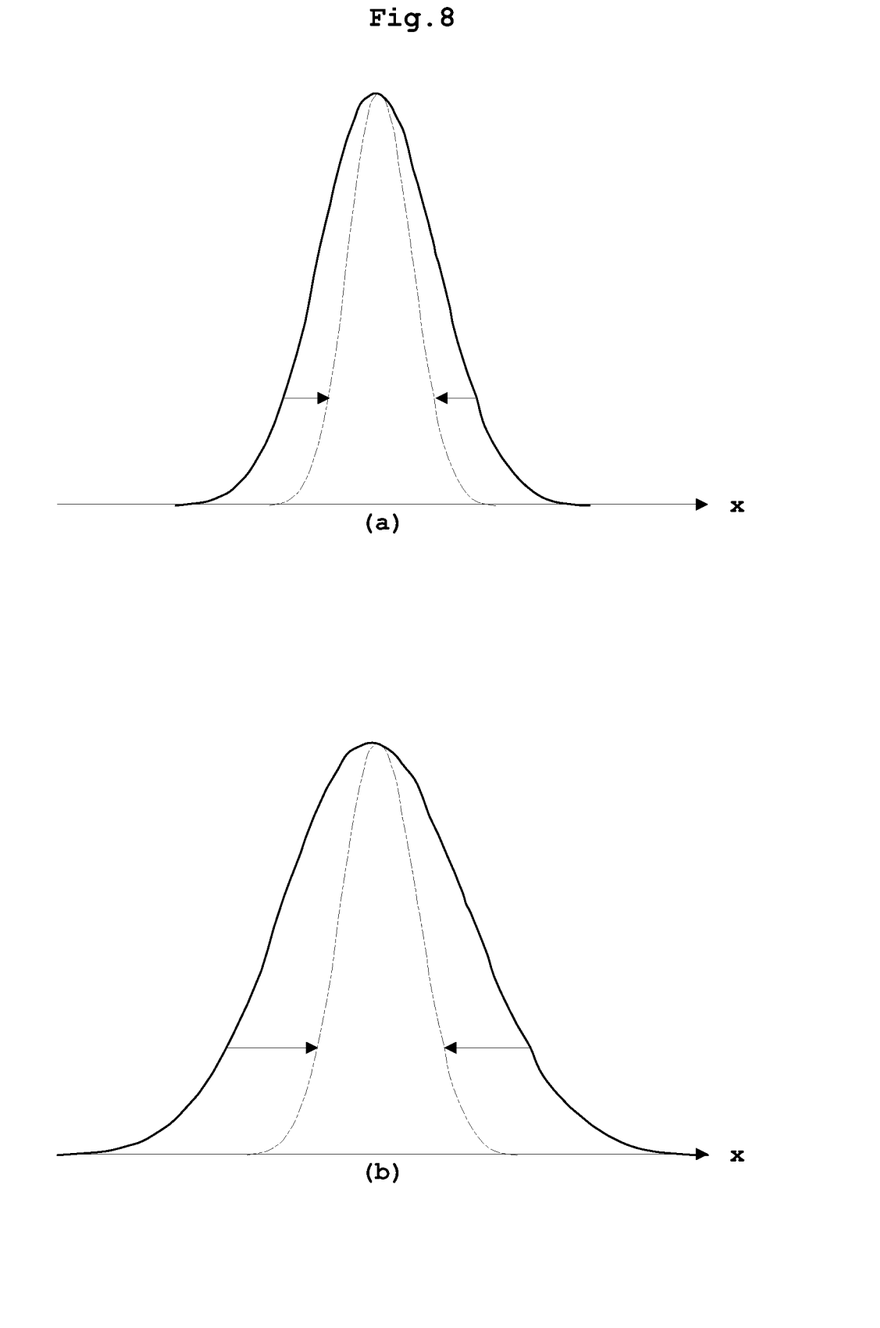

Next, specific functions of the input unit 6, system matrix calculating unit 10 and reconstruction unit 11 will be described with reference to FIGS. 3-8. FIG. 3 is a flow chart showing a sequence of a reconstruction method including a reconstructing step. FIG. 4 is a schematic view showing coincidence counting in the gamma-ray detectors, which illustrates detection probability. FIG. 5 is a schematic view showing a positional relationship with the gamma-ray detectors when a point source is disposed. FIG. 6 is a schematic view illustrating distances from the gamma-ray detectors, voxels, LORs and point source when the point source is drawn together. FIG. 7 is a graph of a profile of the number (count value) of photons with respect to the distances from the point source and results of fitting (adjustment) of a point spread function (PSF). FIG. 8 is a schematic view illustrating adjustment of the distance range of the point spread function (PSF). FIGS. 4-6 depict only the scintillator blocks 31 as the gamma-ray detectors 3, omitting the light guides 32 and PMTs 33.

Assume that, as shown in FIG. 4, gamma ray photons having generated from voxel $v_j$ are detected on an i-th LOR ($L_i$) with a probability $a_{ij}$. In order to determine this detection probability as shown in FIG. 5, a point source RI is set in a field of view FOV. The point source RI is controlled movable within the field of view FOV, and is controlled movable also in the direction of depth with respect to the plane of FIG. 5. While FIG. 5 shows the respective gamma-ray detectors 3 arranged in an annular form, this is not limitative but they may be arranged in a polygonal form as long as they are arranged in a ring form to surround the subject M. The point source RI corresponds to the point source in this invention.

The length of the i-th LOR ($L_i$) intersecting the field of view FOV (intersection length) is set to $l_i$ as shown in FIG. 6, and the sensitivity of the detection pair of gamma-ray detectors 3 detecting the LOR ($L_i$) is set to $S_i$. Then, a sum total of detection probabilities $a_{ij}$ for voxels $v_j$ (j=0, 1, . . . , J−1) traversed by the LOR ($L_i$) (that is, $\Sigma a_{ij}$ (sum total of $a_{ij}$ from j=0, 1, to . . . )) is expressed by the following equation (1):

[Math 1]

$$\sum_{j=0}^{J-1} a_{ij} = S_i \cdot l_i \quad (1)$$

In the above equation (1), the sum total ($\Sigma a_{ij}$) of detection probabilities $a_{ij}$ for voxels $v_j$ (j=0, 1, . . . , J−1) is expressed by a product of sensitivity $S_i$ and intersection length $l_i$. The sensitivity $S_i$ is obtained by actual measurement, and the intersection length $l_i$ is obtained geometrically. Therefore, the right-hand side of the above equation (1) is known, and the sum total ($\Sigma a_{ij}$) of detection probabilities $a_{ij}$ which is the left-hand side of the above equation (1) also becomes known. Then, in order to obtain each detection probability $a_{ij}$, a provisional detection probability $a'_{ij}$ is obtained first.

(Step S1) Placement of Point Source

In order to obtain the provisional detection probability $a'_{ij}$, the point source RI is placed in the field of view FOV as shown in FIG. 5. Specifically, as shown in FIG. 6, the point source RI is placed in the position of voxel $v_j$, and radiation of the same type as the positron-emitting drug is emitted from the point source RI.

(Step S2) Observation of Number of Photons

Assuming that, at this time, an axis (see the dotted line in FIG. 6) perpendicular to the LOR ($L_i$) has a distance x from the point source RI (that is, a shift from the point source) as shown in FIG. 6, observation is made of a profile of the number (count value) of photons of the radiation with respect to the distance x from the point source RI. Ideally, gamma-ray detectors 3 other than the gamma-ray detectors 3 detecting the LOR ($L_i$) emitted from the point source RI should not detect the radiation. In practice, however, gamma-ray photons spread spatially, and gamma-ray photons are observed also in parts other than where the distance x is "0" (that is, placement location of the point source RI). The profile of the number (count value) of photons measured with respect to the distance x from the point source RI is indicated by rhombuses shown in FIG. 7.

(Step S3) Fitting of PSF

The point spread function (PSF) expressed by the Gauss function is adjusted by fitting it to the profile of the number of photons with respect to the distance x from the point source RI shown in FIG. 7. Each parameter of the Gauss function is adjusted so that the solid line ride on the rhombuses shown in FIG. 7. When, for example, the Gauss function is expressed by $\alpha \exp\{-(x-b)^2/2c^2\}$, the PSF is fitted by adjusting parameters $\alpha$, b and c. Since the detection probability $a_{ij}$ and provisional detection probability $a'_{ij}$ should only be proportional to the PSF, $\alpha$ showing amplitude is not very important. Therefore, the Gauss function is not limited to $\alpha \exp\{-(x-b)^2/2c^2\}$, but may, for example, be $\exp\{-(x-\mu)^2/\sigma^2\}$. A Gauss function may be prepared, which has a separate parameter set for each of the right half (positive direction) and the left half (negative direction) of the distance x. The Gauss function will be described hereinafter, taking for example the case of being expressed by $\alpha \exp\{-(x-b)^2/2c^2\}$.

For the fitting of the PSF (i.e. adjustment of the parameters), the operator carries out the fitting of the PSF manually by inputting values of the parameters through the input unit 6 (see FIG. 1). Specifically, values of the parameters may be inputted directly, or values of the parameters may be inputted by outputting and displaying FIG. 7 on the monitor of the output unit 7 (see FIG. 1) and dragging the solid line to the parts of the rhombuses with the pointing device of the input unit 6. This step S3 corresponds to the function adjusting step in this invention.

(Step S4) Adjustment of Distance Range

What is different from Nonpatent Document 4 noted hereinbefore is that $a_{ij}$ is not obtained by reducing the spread of the PSF by a fixed quantity. In this step S4, the provisional detection probability $a'_{ij}$ is obtained by adjusting the distance range of the PSF for each layer in the depth direction of the gamma-ray detectors 3 indicating an incident direction in which the radiation strikes. Preferably, for a layer shallow in the depth direction of the gamma-ray detectors 3 shown in FIG. 8 (a), the distance range is not adjusted, or the distance range is adjusted by reducing it slightly (the solid line indicating the range before the adjustment, and the chain line after the adjustment). For a back layer in the depth direction of the gamma-ray detectors 3 shown in FIG. 8 (b) the distance range is adjusted by reducing it greatly (the solid line indicating the range before the adjustment, and the chain line after the adjustment).

A value of adjustment of the distance range may be based on empirical rule, or when the operator determines in step S8 described hereinafter that an image obtained by the reconstruction in step S7 described hereinafter is inappropriate, as shown in this flow of FIG. 3, the operation may return to step S4 to infer a value of adjustment of the distance range again from actual pixel values. In order to adjust the distance range, the operator adjusts the distance range manually by inputting a value of adjustment of the distance range through the input unit 6 (see FIG. 1). Specifically, a value of adjustment of the distance range may be inputted directly, or a value of adjustment may be inputted by outputting and displaying FIG. 8 on the monitor of the output unit 7 (see FIG. 1) and dragging the solid line to the area of the chain line with the pointing device of the input unit 6. This step S4 corresponds to the distance range adjusting step in this invention.

(Step S5) Phantom Radiography for Evaluation

Here, a phantom for evaluation is prepared afresh and radiography is carried out with the gamma-ray detectors 3.

(Step S6) System Matrix Calculation

The system matrix calculating unit 10 (see FIG. 1) calculates $a_{ij}$ which is an element in the system matrix using the phantom for evaluation based on the PSF having the distance range adjusted in step S4. First, assuming that the PSF (Gauss function $\alpha\exp\{-(x-b)^2/2c^2\}$ here) having the distance range adjusted is equal to the provisional detection probability the provisional detection probability $a'_{ij}$ is derived from the following equation (2). The right side of the following equation (2) is assumed to be the PSF having the distance range adjusted.

[Math 2]

$$a'_{ij} = \alpha\exp[-(x-b)^2/2c^2] \quad (2)$$

Since the detection probability finally obtained is proportional to the PSF (provisional detection probability $a'_{ij}$) having the distance range adjusted, the sum total (that is, $S_i \cdot l_i$ which is the product of sensitivity $S_i$ and intersection length $l_i$) of detection probabilities $a_{ij}$ of equation (1) noted above is considered also proportional with the same ratio as the sum total of provisional detection probabilities $a'_{ij}$ (that is, $\Sigma a'_{ij'}$ (j'=0, 1, . . . to $a'_{ij}$)) in the above equation (2). Therefore, detection probability is expressed by the following equation (3) using the PSF having the distance range adjusted (provisional detection probability $a'_{ij}$), the sum total ($\Sigma a'_{ij'}$) of provisional detection probabilities $a'_{ij'}$, and $S_i \cdot l_i$ which is the product of sensitivity $S_i$ and intersection length $l_i$ in the above equation (1).

[Math 3]

$$a_{ij} = \frac{a'_{ij}}{\sum_{j'=0}^{J-1} a'_{ij'}} \cdot S_i \cdot l_i \quad (3)$$

As is clear from equation (3) above, when the Gauss function is expressed by $\alpha\exp\{-(x-b)^2/2c^2\}$, since $\alpha$ indicating amplitude is reduced and canceled, adjustment is not necessarily required for $\alpha$ in step S3. From equation (3) above, detection probabilities $a_{ij}$ are obtained based on the PSF having the distance range adjusted in step S4. This step S6 corresponds to the system matrix calculating step in this invention.

(Step S7) Reconstruction

The reconstruction unit 11 (see FIG. 1) carries out reconstruction based on the system matrix obtained by the system matrix calculating unit 10. The reconstruction based on the system matrix will be described with reference to Nonpatent Document 1 noted hereinbefore. Here, description will be made with application of a list-mode DRAMA method (Dynamic Row-Action Maximum Likelihood Algorithm). In the list-mode DRAMA method, an image is reconstructed using data of gamma-ray photons observing events in time series.

The total of events detected by the gamma-ray detectors 3 is set to T, and an LOR corresponding to the t-th event (t=0, 1, . . . , T−1) to i(t). Each event is divided into L subsets $S_l$ (l=0, 1, . . . , L−1). Regarding each voxel $v_j$ (j=0, 1, . . . , J−1), pixel values immediately before and immediately after a pixel value renewal for an l-th subset in a k-th (k=0, 1, . . . ) iteration are set to $x_j^{(k, l)}$ and $x_j^{(k, l+1)}$, respectively.

When random and scatter events and the effect of absorption are disregarded, a renewal equation for pixel value $x_j^{(k, l)}$ is expressed by following equations (4):

[Math 4]

$$x_j^{(k,l+1)} = x_j^{(k,l)} \left\{ \frac{1 + \frac{\lambda^{(k,l)}}{C_j} \cdot \sum_{t \in S_l} a_{i(t)j}}{\left(\frac{1}{\sum_{j'=0}^{J-1} a_{i(t)j'} x_{j'}^{(k,l)}} - p_{lj}\right)} \right\} \quad (4)$$

$$\lambda^{(k,l)} = \beta_0 / (\beta_0 + l + \gamma kl),$$

$$C_j = \max \sum_{t \in S_l} a_{i(t)j} p_{lj},$$

$$x_j^{(k+1,0)} = x_j^{(k,L-1)}$$

$\lambda^{(k, l)}$ in the above equations (4) is a relaxation parameter, and $C_j$ in the above equations (4) is a normalization matrix. $p_{lj}$ is called "Blocking Factor", which may be selected arbitrarily, and this embodiment uses Blocking Factor A with $p_{lj}$ not dependent on l (see the following equation (5)).

[Math 5]

$$p_{lj} = \sum_{i=0}^{l-1} a_{ij} / L \quad (5)$$

First, $a_{ij}$ is added for all possible LORs (the number being about $N_C{}^2/2$), to obtain $\Sigma a_{ij}$ (sum total of $a_{ij}$ from j=0, 1, to . . . ). $\Sigma a_{ij}$ is an image equal in size with a reconstructed image (reconstruction image), which expresses a probability of voxel $v_j$ being detected by one of the LORs, and so is called "sensitivity distribution map". By using this sensitivity distribution map, $C_j$ and $p_{lj}$ in the above equations (4) can be obtained.

Specifically, $x_j^{(0, 0)}$ which is an initial image is set as appropriate. The initial image $x_j^{(0, 0)}$ may be an image having a uniform pixel value, for example, which may be $x_j^{(0, 0)} > 0$. The set initial image $x_j^{(0, 0)}$ and $a_{ij}$ calculated in step S6 ($a_{i(t)j}$ since i→i(t) in the above equations (4)) are used, and by repeatedly substituting them into the above equations (4), $x_j^{(0, 0)}, \ldots, x_j^{(0, L-1)}$ are obtained successively. $x_j^{(0, L-1)}$ finally obtained is made $x_j^{(1, 0)}$ to raise it to $x_j^{(1, 0)}$. Similarly thereafter $x_j$ is raised in order ($x_j^{(0, 0)}, x_j^{(1, 0)}, \ldots, x_j^{(k, 0)}$). There is no limitation to the number of times of k which expresses iteration, but it may be set as appropriate. The reconstruction unit 11 (see FIG. 1) carries out reconstruction by arranging $x_j$ finally obtained for each corresponding voxel $v_j$, to obtain an image of the phantom for evaluation. This step S7 corresponds to the reconstructing step in this invention.

The reconstruction based on the system matrix is not limited to the DRAMA method described above, but may use static RAMLA (Row-Action Maximum Likelihood Algorithm), ML-EM (Maximum Likelihood Expectation Maximization), or OSEM (Ordered Subset ML-EM). It is preferred to carry out reconstruction using iterative approximation using iterative approximation equations like the above equations (4).

(Step S8) Image OK?

The operator determines whether the image obtained by the reconstruction in step S7 is inappropriate or not. When, for example, an overcorrection phenomenon (e.g. a ringing adjacent boundaries of the phantom for evaluation) appears in the image obtained by the reconstruction in step S7, the operator determines that the image is inappropriate, and the operation returns to step S4 to adjust the distance range of the PSF again. When the image obtained by the reconstruction in step S7 is appropriate, the operation moves to the next step S9 to carry out radiography and reconstruction of an actual subject M (small animal here).

(Step S9) Radiography and Reconstruction of Actual Subject

The radiography and reconstruction of the actual subject M is carried out using the PSF with the distance range adjusted in step S4. For the radiography and reconstruction of the actual subject M, the same calculations are carried out as in steps S6 and S7, except that the phantom for evaluation is replaced by the actual subject M, and their description is omitted. In this way, the series of reconstruction (steps S1-S9) is ended.

According to the PET apparatus 1 in this embodiment having the above construction, when obtaining the system matrix (detection probability $a_{ij}$) (step S6), adjustment is made through the input unit 6 by fitting the point spread function (PSF) expressed by the Gauss function, to the profile of the number (count value) of photons with respect to the distance x from the point source RI which emits radiation of the same type as the positron-emitting drug (step S3). Adjustment is made through the input unit 6 of the distance range of the PSF for each layer in the depth direction of the gamma-ray detectors 3 indicating an incident direction in which the radiation strikes (step S4). Considering that the spread of counts of the radiation changes for each layer, the gap is thought to decrease by adjusting the distance range (e.g. full width at half maximum (FWHM) or distribution) of the PSF expressed by the Gauss function. Thus, image quality of a reconstructed image can be improved by adjusting the distance range of the PSF for each layer to obtain the system matrix (detection probability $a_{ij}$).

In this embodiment, in order to take into consideration the larger statistical errors occur with geometric calculations and reconstruction data at the time of reconstruction for the deeper layers in the depth direction of the gamma-ray detectors 3, it is preferred that the adjustment is made by reducing the distance range by a progressively larger extent for positions becoming deeper in the depth direction of the gamma-ray detectors 3. That is, it is thought that the spread of counts of the radiation is small for layers shallow in the depth direction of the gamma-ray detectors 3, and that the spread of counts of the radiation is large for layers deep in the depth direction. Therefore, the gap is thought to decrease when the distance range is not adjusted, or the distance range is adjusted by slightly reducing it as shown in FIG. 8 (*a*), for layers shallow in the depth direction of the gamma-ray detectors 3, and the distance range is adjusted by reducing it by a progressively large extent for positions becoming deeper in the depth direction of the gamma-ray detectors 3 as shown in FIG. 8 (*b*).

In this embodiment, when adjusting the distance range in step S4 (which corresponds to the distance range adjusting step in this invention), the distance range of the PSF for each layer is adjusted based on results reconstructed only of signals of applicable layers of the gamma-ray detectors 3 (image obtained by reconstruction in step S7 here).

Figure 9:
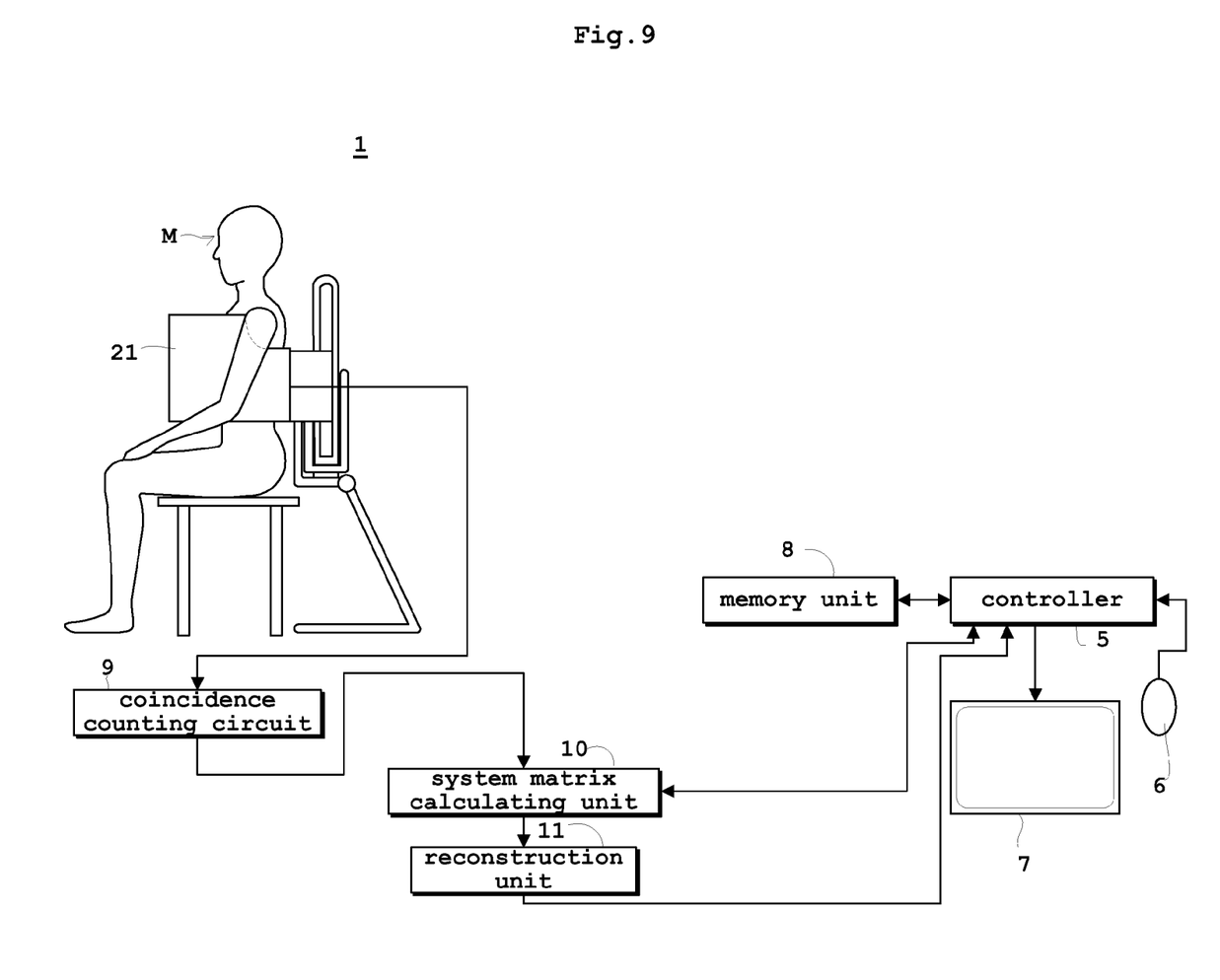
FIG. 9 is a side view and block diagram of a mammographic apparatus according to a modified embodiment.
Figure 10:
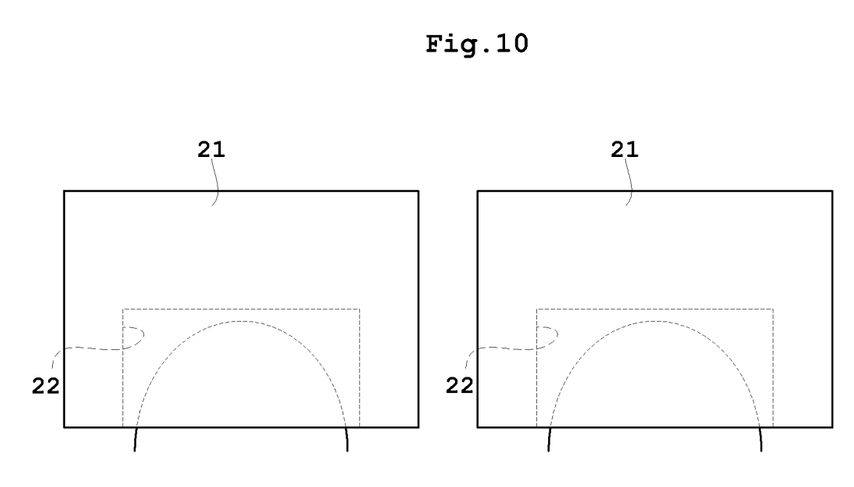
FIG. 10 is a plan view of a breast examining unit of a mammographic apparatus according to a further modified embodiment.

This invention is not limited to the foregoing embodiment, but may be modified as follows:

(1) The foregoing embodiment has been described taking a small animal (e.g. a mouse) as an example of subjects, and a PET apparatus for small animals as an example of PET apparatus. However, the invention may be applied to PET apparatus for particular body parts. The PET apparatus for particular body parts, when the subject is a human body, for example, include a mammography apparatus (see FIG. 9 or FIG. 10) for radiographing the breasts of the human body. It has the same construction as in FIG. 1, excepting that the gantry in FIG. 1 is replaced by a breast examining unit 21 as shown in FIG. 9 or FIG. 10. In the case of FIG. 9, the breast examining unit 21 is in form of a cutout, and the breasts are examined as placed in this cutout and held between the arms. The plurality of gamma-ray detectors 3 (not shown in FIG. 9) are arranged in the breast examining unit 21 in conformity with this cutout. In the case of FIG. 10, as shown in the plan view of FIG. 10, the breast examining unit 21 is in form of boxes with openings 22 for receiving the breasts. Similarly, the plurality of gamma-ray detectors 3 (not shown in FIG. 10, either) are arranged in the breast examining unit 21 in conformity with these openings 22. This invention is useful for apparatus where the subjects of examination are small and require resolution capability, like the PET apparatus for small animals as in the foregoing embodiment and the PET apparatus for particular body parts as in this modification (1).

(2) The foregoing embodiment and the modification (1) have been described taking for example the apparatus where the subjects of examination are small and require resolution capability. However, the invention may be applied to PET apparatus for scanning large subjects of examination. The invention may be applied, when the subject is a human body, for example, to a PET apparatus for scanning the whole body of the subject. When the subject is a human body, the invention may be applied to a PET apparatus for radiographing the head of the subject.

(3) In the foregoing embodiment, the function adjusting device and distance range adjusting device in this invention are the input unit 6, and each adjustment is carried out manually. However, the function adjusting device and distance range adjusting device in this invention may be in form of the controller 5 to carry out each adjustment automatically, such that a value of each adjustment and pixel values are matched to each other, and the controller 5 carries out arithmetic processing of the value of each adjustment based on the pixel values to obtain pixel values again. Both the manual operation and automatic operation may be combined.

(4) In the foregoing embodiment, the respective gamma-ray detectors are arranged in a ring form, but the configuration is not limited to the ring form. The configuration may be as shown in FIG. 9 or FIG. 10 described above.

(5) In the foregoing embodiment, the distance from the point source is determined along an axis perpendicular to a LOR ($L_i$) as shown in FIG. 6. As long as the distance from the point source is expressed, it is not limited to the distance shown in FIG. 6. As in Nonpatent Document 3 noted hereinbefore, for example, each gamma-ray detector in the circumferential direction p with respect to the gamma-ray detectors which are targets of detection may be determined as the distance from the point source.

DESCRIPTION OF REFERENCES

1 . . . PET apparatus
3 . . . gamma-ray detectors
6 . . . input unit
9 . . . coincidence counting circuit
10 . . . system matrix calculating unit
11 . . . reconstruction unit
$a_{ij}$ . . . probability (system matrix)
x . . . distance
RI . . . point source

The invention claimed is:

1. A positron CT apparatus having:
a plurality of detectors for detecting radiation released from a positron-emitting drug given to a subject, and outputting electric signals;
a coincidence counting circuit for detecting, based on the electric signals, that a simultaneous observation of the radiation is made in two of the detectors;
a system matrix calculating device for calculating a system matrix based on outputs of the coincidence counting circuit; and
a reconstructing device for generating a distribution image of the positrons as an image based on the system matrix;
the positron CT apparatus comprising:
a function adjusting device for making adjustment by fitting a point spread function to a profile of count values of radiation with respect to a distance from a point source which emits radiation of the same type as the positron-emitting drug; and
a distance range adjusting device for adjusting a distance range of the function for each layer in a depth direction of the detectors indicating an incident direction in which the radiation strikes;
wherein the system matrix is calculated based on the function with the distance range adjusted.

2. The positron CT apparatus according to claim 1, wherein the function adjusting device comprises an input unit, and the adjustment is carried out manually by input to the input unit.

3. The positron CT apparatus according to claim 1, wherein the distance range adjusting device comprises an input unit, and the adjustment is carried out manually by input to the input unit.

4. The positron CT apparatus according to claim 1, wherein the function adjusting device comprises a controller, and the adjustment is carried out automatically by arithmetic processing of the controller.

5. The positron CT apparatus according to claim 1, wherein the distance range adjusting device comprises a controller, and the adjustment is carried out automatically by arithmetic processing of the controller.

6. The positron CT apparatus according to claim 1, wherein the detectors are DOI detectors having a plurality of layers in the depth direction.

7. The positron CT apparatus according to claim 1, wherein the respective detectors are arranged in a ring form to surround the subject.

8. The positron CT apparatus according to claim 1, wherein:
the subject is a small animal; and
the positron CT apparatus is a PET apparatus for small animals.

9. The positron CT apparatus according to claim 1, wherein:
the subject is a human body; and
the positron CT apparatus is a PET apparatus for scanning a whole body of the subject.

10. The positron CT apparatus according to claim 1, wherein:
the subject is a human body; and
the positron CT apparatus is a PET apparatus for the head for radiographing the head of the subject.

11. The positron CT apparatus according to claim 1, wherein:
the subject is a human body; and
the positron CT apparatus is a PET apparatus for particular body parts for radiographing particular body parts of the subject, respectively.

12. The positron CT apparatus according to claim 11, wherein the PET apparatus for particular body parts is a mammography apparatus for radiographing the breasts of the subject.

13. The positron CT apparatus according to claim 12, wherein:
a breast examining unit is provided in form of a cutout for examining the breasts as placed in the cutout and held between the arms; and
the plurality of detectors are arranged in the breast examining unit in conformity with the cutout.

14. The positron CT apparatus according to claim 12, wherein:
a breast examining unit is provided in form of boxes for examining the breasts, the breast examining unit having openings for receiving the breasts; and
the plurality of detectors are arranged in the breast examining unit in conformity with the openings.

15. A reconstruction method for generating a distribution image of positrons as an image based on radiation released from a positron-emitting drug given to a subject, the reconstruction method comprising a series of:
(a) a function adjusting step for making adjustment by fitting a point spread function to a profile of count values of radiation with respect to a distance from a point source which emits radiation of the same type as the positron-emitting drug;
(b) a distance range adjusting step for adjusting a distance range of the function for each layer in a depth direction of detectors indicating an incident direction in which the radiation strikes;
(c) a system matrix calculating step for calculating a system matrix based on the function with the distance range adjusted; and
(d) a reconstructing step for generating the distribution image of the positrons as an image based on the system matrix.

16. The reconstruction method according to claim 15, wherein the adjustment is made by reducing the distance range by a progressively larger extent for positions becoming deeper in the depth direction of the detectors.

17. The reconstruction method according to claim 15, wherein based on results of reconstruction of each layer in the depth direction of the detectors, the distance range adjusting step adjusts the distance range of the function for each layer.

18. The reconstruction method according to claim 15, wherein the distance from the point source is determined along an LOR which is a virtual straight line linking two of the detectors that carry out coincidence counting.

19. The reconstruction method according to claim 15, wherein each detector in a circumferential direction with respect to the detectors which are targets of detection is determined as the distance from the point source.

20. The positron CT apparatus according to claim 1, wherein the point spread function is expressed by a Gauss function.

21. The reconstruction method according to claim 15, wherein the point spread function is expressed by a Gauss function.

* * * * *